United States Patent [19]

Larsson et al.

[11] Patent Number: 4,666,427
[45] Date of Patent: May 19, 1987

[54] FLUID AND PARTICLE ABSORBING BODY FOR APERTURES IN INJECTION INSTRUMENTS

[75] Inventors: Nils E. Larsson, Helsingborg; Kaj O. Stenberg, Staffanstorp, both of Sweden

[73] Assignee: Viggo AB, Helsingborg, Sweden

[21] Appl. No.: 810,138

[22] Filed: Dec. 18, 1985

[30] Foreign Application Priority Data

Dec. 27, 1984 [SE] Sweden .............................. 8406614

[51] Int. Cl.⁴ .............................................. A61M 5/00
[52] U.S. Cl. ...................................... 604/51; 604/126; 604/256
[58] Field of Search .................. 604/126, 45, 51, 122, 604/251, 252, 256

[56] References Cited

U.S. PATENT DOCUMENTS

| | | | |
|---|---|---|---|
| 3,578,037 | 5/1971 | Flynn | 604/51 |
| 3,778,971 | 12/1973 | Granger et al. | 604/126 |
| 3,834,124 | 9/1974 | Ichikawa | 604/126 |
| 4,250,879 | 2/1981 | Muetterties | 604/126 |
| 4,440,207 | 4/1984 | Genatempo et al. | 604/256 |
| 4,484,916 | 11/1984 | McPhee | 604/256 |

FOREIGN PATENT DOCUMENTS 0093063 6/1982 Japan .................................. 604/126

Primary Examiner—Stephen C. Pellegrino
Attorney, Agent, or Firm—Beveridge, DeGrandi & Weilacher

[57] ABSTRACT

A method for reducing the risk of particle (bacteria) contamination of parts of the body or body fluids by entraining particles in a fluid injected in the part of the body or body fluid by means of a fluid supplying instrument through a fluid inlet associated therewith is characterized in that after injection of the fluid through the fluid inlet, a fluid- and particle-absorbing, vapor-permeable body is inserted in the inlet so as to be exposed with the instrument, while an instrument, such as a cannula, catheter etc., for introducing fluid in parts of the body or body fluids is characterized in that such a fluid- and particle-(bacteria-) absorbing body is provided in the fluid inlet of the instrument.

13 Claims, 1 Drawing Figure

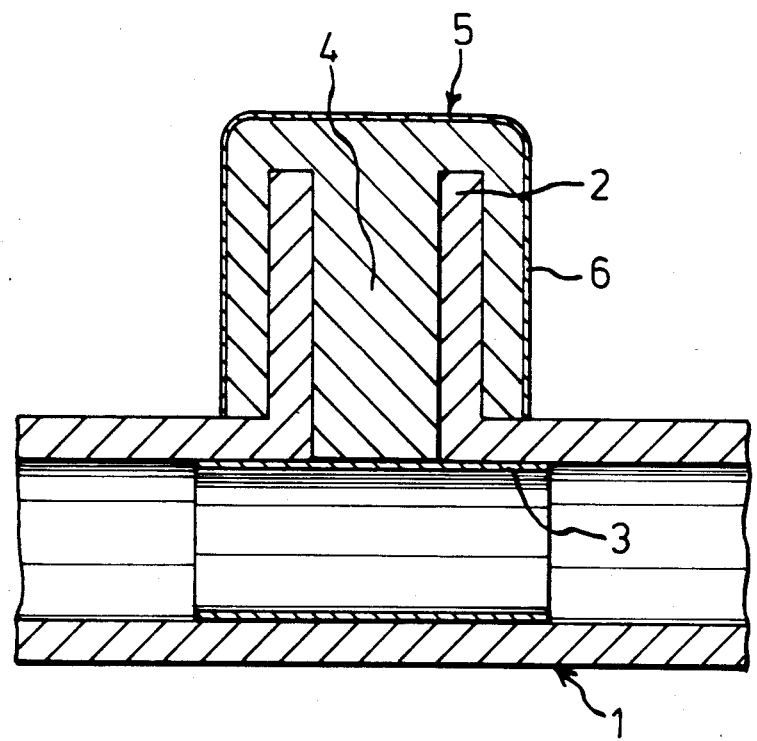

FLUID AND PARTICLE ABSORBING BODY FOR APERTURES IN INJECTION INSTRUMENTS

The present invention relates to a method for reducing the risk of particle contamination of parts of the body or body fluids by entraining particles in a fluid which is injected in the part of the body or body fluid by means of a fluid supplying instrument through a fluid inlet associated therewith.

Many infusion cannulae have an injection port which is connected to the cannula bore and through which a medical solution can be applied to a patient, often in admixture with the primary solution which is fed to the cannula bore through the patient distal end thereof. The injection port is often controlled by a valve which is disposed in the area of the mouth of the port opening in the cannula bore and which is opened under the action of the injection pressure of the solution supplied through the port by means of a hypodermic syringe.

After the solution has been injected, the syringe is retracted from the port and the valve closes the port. It has been noted that a small residual volume of the solution coming from the syringe most often remains in the port upstream of the valve, which is probably due to surface tension phenomena and insufficient valve opening pressure during the final phase of the injection. Such a residual volume may be the course of particle (bacteria) contamination of the patient when, upon a renewed injection of solution through the injection port, it is flushed into the patient.

The object of the invention is to solve this problem, which is achieved by inserting a fluid- and particle-absorbing, vapour-permeable body in the fluid inlet after an injection has been performed therethrough.

The effect achieved by the invention is surprising. The reason for this is that the bacteria absorbed in the absorbent body together with the residual fluid will die when the absorbed residual fluid evaporates at the surface of the body which is exposed to the surrounding atmosphere. If the injected fluid is isotonic, a further bactericidal effect is obtained in that salt from the isotonic residual fluid, during the evaporation thereof through the porous body, precipitates in the pores of the body and causes bacteria denaturation.

In this context, "particles" primarily relates to bacteria, but it will be evident that other types of particles are also comprised by the inventive scope.

The fluid absorbing body may contain a bactericide for destroying any surviving bacteria in the residual volume absorbed. Experiments have however shown that this is not necessary in most cases.

The absorbent body is advantageously provided with a gripping and protective member which is located outside the entrance opening of the port when the body is applied in the port. This protective member which may be a plastic sleeve placed with press fit over one end of the body (upper end when in use) serves to preclude any contact with the body when being gripped. This may be to particular advantage if the fluid absorbing body is used as a port cover and is left in the port until the next injection should be performed. This protective member should be provided with an aperture or apertures through which liquid absorbed in the body can evaporate into the surrounding atmosphere.

If the port is provided with a conventional cover, it is possible after an injection to remove the body from the port and discard it, the port being closed by the cover.

The fluid- and bacteria-absorbing body may consist of any conventional material for liquid and bacteria absorption but should be non-crumbling and, suitably, sterilised. An example of a suitable starting material for the body is hydrophilic or hydrophilated porous plastic, such as polyethylene manufactured by POREX® Technologies, Fairborn, USA, as moulded bodies of optional pore diameter, preferably 10–250 $\mu$m for a pore volume of 30–70% of the total volume of the body. Another example is a gelling material, such as starch, gel, for instance JODOSORB® from Perstorp Aktiebolag, Sweden, containing an iodine/dextrin complex which can be enclosed in a cup-shaped stiff sleeve provided with apertures as described above. A further example are cellulosic fiber materials.

The absorbent body may also consist of a composite material which is made up of layers of material having different absorbency, and may be provided on its surface exposed to the atmosphere, with a thin membrane permeable to vapour but not to bacteria. Such membranes are available on the market as sterile filters having pores of about 0.1–1.0 $\mu$m.

Although the invention has been described above in connection with the injection port of a cannula, it will be understood that it is also applicable to other apertures, both inlet and outlet apertures, in medical instruments, such as catheter (luer) connections etc., through which a fluid is supplied to a patient.

One embodiment of the invention will now be described in greater detail hereinbelow with reference to the accompanying drawing which is a sectional view, with parts broken away, of a cannula equipped with a fluid- and bacteria-absorbing body.

In the FIGURE, there is shown a conventional cannula 1 having an injection port 2 and an injection port valve 3. In the port 2, there is inserted with a relatively tight fit a plug 4 which consists of porous hydrophilated polyethylene having pores of about 50 $\mu$m and which is here integrated in a cap 5, such that the part has its external side surrounded and its top face covered by a flange formed integrally with the plug. A thin sterile filter 6 is mounted on the outer side of the cap. Both the plug 4 and the filter 6 are vapour-permeable, while the filter 6 is bacteria-impermeable.

With the top of the cannula inserted in the patient and with the cap 5 removed from the port 2, a solution is injected in the cannula bore through the port 2. After completion of the injection and withdrawal of the syringe, the cap is again placed on the port 2 for absorbing, by means of the plug 4, the residual volume of solution and any bacteria present therein.

Tests have been carried out with a view to studying the capacity of the fluid- and particle-absorbing body according to the invention to absorb residual fluid so as to prevent bacteria growth. The tests were carried out on five cannulae of the type illustrated in the FIGURE, using a suspension of the bacterium *Staf aureus* NCTC 8532 in a concentration of $10^3$/ml and a POREX® plug as shown in the FIGURE, however without a sterile filter 6.

In the injection ports, 20 $\mu$l (about 600 bacteria) of the suspension was injected, whereupon the plugs were inserted in the ports. The cannulae were then kept at 35° C. in heating cabinets overnight. The next morning each injection port was rinsed five times with 100 ml of sterile soybean broth (nutrient solution), whereupon another 20 $\mu$l of the suspension was injected in the port and the pertaining plug was again placed in the port.

The rinsing liquid was poured in test tubes containing 3 ml of sterile soybean broth and being placed in heating cabinets at 35° C. This procedure was repeated for five days. The growth in said quantity of soybean broth was checked every day by means of conventional turbidity measurements. No growth (turbidity) of said bacteria could be detected in said quantity of soybean broth (rinsing liquid+added sterile soybean broth) at any time.

The test described above was repeated with the difference that the amount of bacteria suspension (20 μl) to be tested was injected in the ports every second hour during the five days of testing, instead of once a day. Otherwise, the same procedure as described above was followed. Nor did this test exhibit any growth of bacteria.

What we claim and desire to secure by Letters Patent is:

1. Method for reducing the risk of bacterial contamination of a patient by a device for administering a fluid to the patient, wherein the method comprises
    providing an aperture in the device into which a fluid can be injected for passage through the device into the patient;
    injecting the fluid into the aperture, through the device, and into the patient;
    closing the aperture with a fluid-absorbing and particle-absorbing, vapor permeable body, wherein the body has an outer surface and at least part of the outer surface is exposed to atmosphere surrounding the device; and
    removing residual fluid in the aperture by evaporation through the outer surface of the body to reduce viability of bacteria in the aperture and the apparatus.

2. Device for administering a fluid to a patient, wherein the device consists essentially of
    conduit means for introducing a fluid into a patient;
    aperture means in the conduit for introducing the fluid into the conduit;
    fluid-absorbing and particle-absorbing, vapor permeable, removable, body means for closing the aperture after the fluid has been introduced into the conduit, wherein the body has an outer surface at least part of which is exposed to atmosphere surrounding the device;
    and wherein the body is sufficiently permeable to permit residual fluid in the aperture to pass through the body into the atmosphere.

3. Device as claimed in claim 2, wherein the body consists of a porous, hydrophilic or hydrophilated material.

4. Device as claimed in claim 3, wherein the body is comprised of plastic material.

5. Device as claimed in any one of claims 3-4, wherein the body has a particle-impermeable, vapour-permeable membrane on its surface exposed to surrounding atmosphere.

6. Device as claimed in claim 5 wherein the body has an apertured protective cap on an end of the body, said cap having a surface exposed to surrounding atmosphere.

7. Device as claimed in claim 2, wherein the device is a cannula provided with an injection port which forms said aperture means in which said body is inserted.

8. Device as claimed in claim 2, wherein the body contains a bactericide.

9. Device as claimed in claim 6, wherein the device is a cannula having an injection port which forms said aperture means in which said body in inserted.

10. Device as claimed in claim 5, wherein the device is a cannula having an injection port which forms said aperture means in which said body is inserted.

11. Cannula for administering a fluid to a patient, wherein the cannula contains a liquid, which is contaminated with bacteria, said cannula consisting essentially of
    conduit means for introducing a sterile fluid into a patient;
    aperture means in the conduit for introducing the sterile fluid into the conduit;
    fluid-absorbing and particle-absorbing, vapor permeable, removable, body means for closing the aperture after the sterile fluid has been introduced into the conduit, wherein the body has an outer surface at least part of which is exposed to atmosphere surrounding the cannula;
    and wherein the body contains the bacteria-contaminated liquid and the body is sufficiently permeable to permit liquid in the aperture to pass out of the cannula through the body and into the atmosphere.

12. Method for reducing the risk of bacterial contamination of a patient by a device for administering a fluid to the patient, wherein the method comprises
    providing an aperture in the device into which a fluid can be injected for passage through the device into the patient;
    injecting the fluid into the aperture, through the device, and into the patient;
    closing the aperture within a fluid-absorbing and particle-absorbing, vapor permeable body, wherein the body has an outer surface and at least part of the outer surface is exposed to atmosphere surrounding the device; and
    removing the vapor permeable body containing residual fluid from the aperture to reduce viability of bacteria in the aperture and the apparatus.

13. Method according to claim 12, which comprises closing the aperture with a cover after removal of the vapor permeable body.

* * * * *